United States Patent
Chen et al.

(10) Patent No.: US 11,135,238 B2
(45) Date of Patent: Oct. 5, 2021

(54) METHODS TO STABILIZE AND REVERSE ATHEROSCLEROTIC LESIONS BY SULFATED POLYSACCHARIDES

(71) Applicant: Morningbell Wellness LLC, Greensboro, NC (US)

(72) Inventors: Chen Chen, Greensboro, NC (US); Miao Zhang, Greensboro, NC (US); Edward Hoyt, Greensboro, NC (US); Kevin Chen, Greensboro, NC (US)

(73) Assignee: Calroy Health Sciences, LLC, Scottsdale, AZ (US)

( * ) Notice: Subject to any disclaimer, the term of this patent is extended or adjusted under 35 U.S.C. 154(b) by 0 days.

(21) Appl. No.: 16/219,854

(22) Filed: Dec. 13, 2018

(65) Prior Publication Data
US 2019/0216844 A1  Jul. 18, 2019

Related U.S. Application Data

(60) Provisional application No. 62/598,839, filed on Dec. 14, 2017, provisional application No. 62/676,185, filed on May 24, 2018.

(51) Int. Cl.
| *A01N 63/00* | (2020.01) |
| *A61K 31/715* | (2006.01) |
| *A61K 31/737* | (2006.01) |
| *A61P 9/10* | (2006.01) |
| *A61K 36/05* | (2006.01) |
| *A61K 9/00* | (2006.01) |
| *A61K 36/87* | (2006.01) |
| *C08B 37/00* | (2006.01) |

(52) U.S. Cl.
CPC .......... *A61K 31/715* (2013.01); *A61K 9/0019* (2013.01); *A61K 9/0053* (2013.01); *A61K 31/737* (2013.01); *A61K 36/05* (2013.01); *A61K 36/87* (2013.01); *A61P 9/10* (2018.01); *C08B 37/00* (2013.01)

(58) Field of Classification Search
CPC .................................................... A01N 63/00
USPC ................................. 424/93.5, 93.51, 195.11
See application file for complete search history.

(56) References Cited

U.S. PATENT DOCUMENTS

| 6,797,705 B2 | 9/2004 | Daniels |
| 7,022,682 B2 | 4/2006 | Daniels |
| 2004/0097466 A1 | 5/2004 | Daniels |
| 2004/0116381 A1 | 6/2004 | Daniels |
| 2004/0170645 A1 | 9/2004 | Daniels |
| 2004/0208893 A1 | 10/2004 | Daniels |
| 2004/0254631 A1 | 12/2004 | Daniels |
| 2005/0196410 A1 | 9/2005 | Daniels |
| 2007/0036821 A1 | 2/2007 | Daniels |
| 2007/0082868 A1 | 4/2007 | Daniels |
| 2013/0273096 A1* | 10/2013 | Daniels ................ A61K 31/737 424/195.17 |
| 2015/0048821 A1 | 2/2015 | Li et al. |

FOREIGN PATENT DOCUMENTS

| EP | 1728507 B1 | 3/2011 | |
| WO | WO-9846588 A2 * | 10/1998 | ........... A61K 31/275 |
| WO | WO-02083155 A1 * | 10/2002 | ........... A61K 31/737 |
| WO | WO 2013052899 A1 | 4/2013 | |

OTHER PUBLICATIONS

Kalanuria, A.A., et al. Vascular Health and Risk Management, vol. 8, pp. 549-561, 2012.*
Kalanuria et al.; "The Prevention and Regression of Atherosclerotic Plaques: Emerging Treatments;" Vascular Health and Risk Management; (Sep. 24, 2012); pp. 549-561; vol. 8; <doi: 10.2147/VHRM.S27764 >.
Stary et al.; "A Definition of Advanced Types of Atherosclerotic Lesions and a Histological Classification of Atherosclerosis: A Report from the Committee on Vascular Lesions of the Council on Arteriosclerosis, American Heart Association;" Circulation; (Sep. 1, 1995); pp. 1355-1374; vol. 92, Issue 5; <doi: 10.1161/01.CIR.92.5.1355 >.
Zhao et al.; "Atherosclerotic Plaque Imaging by Carotid MRI;" Current Cardiology Reports; (Jan. 2009). pp. 70-77; vol. 11, Issue 1.
Zhao et al.; "Chinese Atherosclerosis Risk Evaluation (CARE II) Study: A Novel Cross-Sectional, Multicentre Study of the Prevalence of High-Risk Atherosclerotic Carotid Plaque in Chinese Patients with Ischaemic Cerebrovascular Events—Design and Rationale;" Stroke and Vascular Neurology; (Jan. 4, 2017); pp. 15-20; vol. 2, e000053; <doi: 10.1136/svn-2016-000053 >.
International Search Report dated Apr. 30, 2019, in International Application No. PCT/US18/65562, filed Dec. 13, 2018; 4 pages.
Li et al.; "Structure and anticoagulant property of a sulfated polysaccharide isolated form the green seaweed *Monostroma angicava*." Carbohydrate Polymers, Applied science publishers; Dec. 6, 2016, pp. 195-206.
Shanmugam et al.; "Heparinoid-active sulphated polysaccharides from marine algae as potential blood anticoagulant agents." Current Science, Indian Academy of Sciences; Dec. 25, 2000; vol. 79, No. 12; pp. 1672-1683.
Yokota et al.; "Fucoidan alleviates high-fat diet-induced dyslipidemia and atherosclerosis in ApoEshlmice deficient in apolipoprotein E expression." The Journal of Nutritional Biochemistry; Elsevier; Jun. 2016; pp. 46-54.

* cited by examiner

*Primary Examiner* — Rodney P Swartz
(74) *Attorney, Agent, or Firm* — Thorpe North & Western, LLP

(57) ABSTRACT

A method of treating a vulnerable atherosclerotic plaque can include identifying the vulnerable atherosclerotic plaque and administering a sulfated polysaccharide, or a pharmaceutically acceptable salt thereof, to a subject in an amount and at a frequency sufficient to stabilize and reverse a vulnerable atherosclerotic plaque.

20 Claims, 1 Drawing Sheet

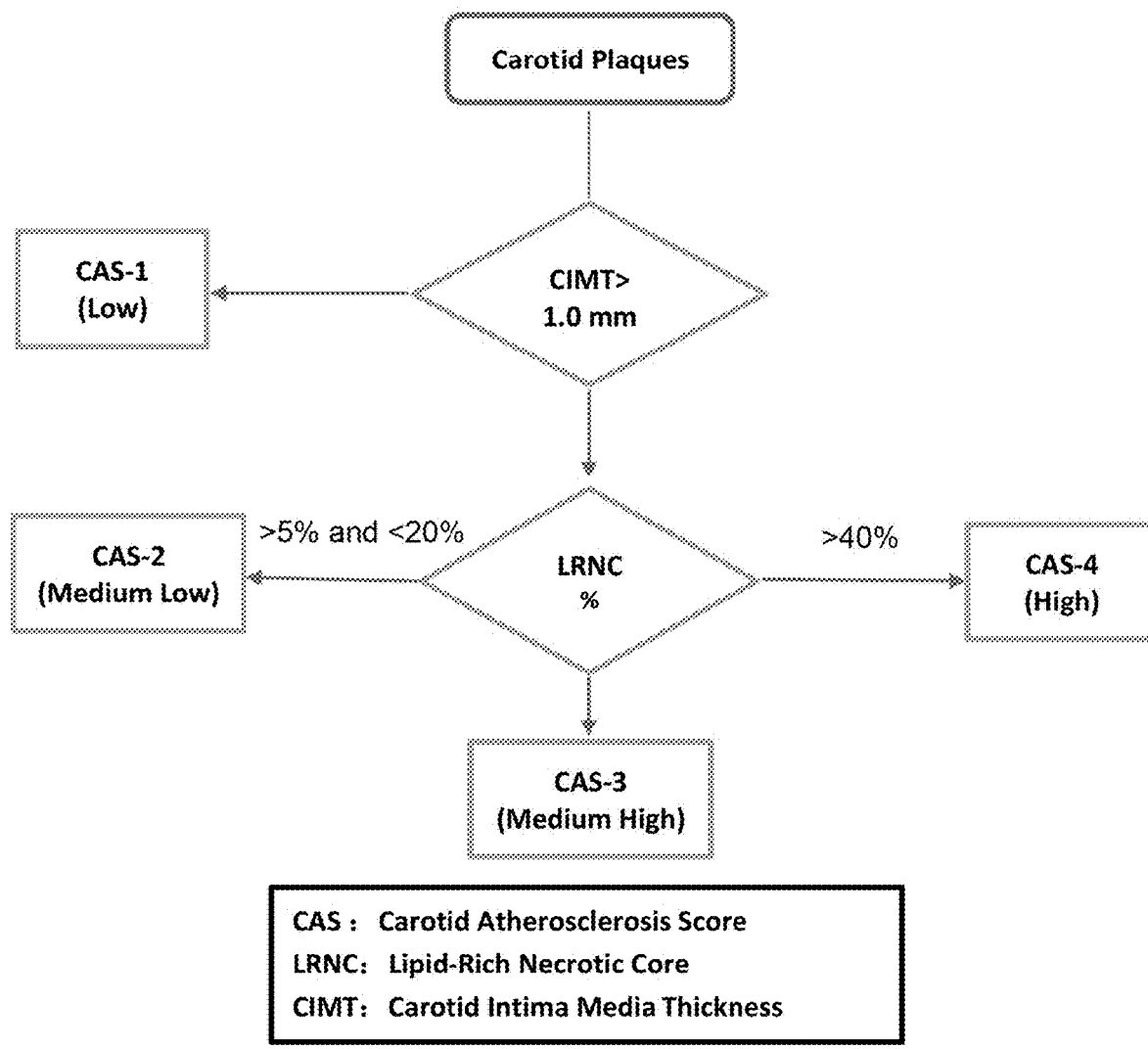

METHODS TO STABILIZE AND REVERSE ATHEROSCLEROTIC LESIONS BY SULFATED POLYSACCHARIDES

RELATED APPLICATIONS

This application claims the benefit of U.S. Provisional Application No. 62/598,839, filed Dec. 14, 2017, and U.S. Provisional Application No. 62/676,185, filed May 24, 2018, which are each incorporated herein by reference.

BACKGROUND

Atherosclerosis is the hardening and thickening of artery walls that can reduce blood flow and cause hypertension, coronary heart disease, carotid artery disease, peripheral artery disease, aneurysms, chronic kidney disease, and erectile dysfunction, among other conditions. The hallmark of atherosclerosis is accumulation of lipids (i.e., cholesterol) on artery walls and a resulting lesion is also called plaque.

An acute cardiovascular, cerebrovascular or peripheral vascular event such as heart attack or stroke follows when an arterial plaque erodes or ruptures. Hence tremendous research and effort have been made to identify the arterial plaques that are prone to erosion and rupture (vulnerable plaque). A vulnerable plaque can be defined as a thrombosis-prone plaque and/or a plaque likely to progress fast, thus becoming a culprit plaque in a future event. The most vulnerable plaques have any or all of the features such as a large lipid-rich necrotic core, an ulcerated and/or a thin fibrous cap, active local inflammation and platelet aggregation, positive remodeling, superficial calcified nodule, neoangiogenesis, and intraplaque hemorrhage which can all lead to plaque rupture and the development of clot. Additionally, lumen size in the vicinity of the plaque lesion is reduced somewhat proportionally in relationship to the lesion size, resulting in restriction of blood flow and increase in hypertension.

Historically, it was thought that atherosclerotic lesion (or plaque) especially the advanced lesion is not reversible. There also has been doubt on the vulnerable plaque theory as it has previously been difficult to identify truly vulnerable plaques. There has been significant uncertainty in how to treat them, except surgical options such as stents. Recent medical advancement has shown that certain drugs such as statins may stabilize atherosclerotic plaques as demonstrated by reducing its lipid-rich necrotic core over long-term treatment. Other approaches including diet and exercise may also help stabilize plaques to a certain extent.

SUMMARY

A method of treating a vulnerable atherosclerotic plaque can include identifying the vulnerable atherosclerotic plaque and administering a sulfated polysaccharide, or a pharmaceutically acceptable salt or metal complex thereof, to a subject in an amount and at a frequency sufficient to stabilize and reverse a vulnerable atherosclerotic plaque.

A therapeutic composition for treating a vulnerable atherosclerotic plaque can include a sulfated polysaccharide, or a pharmaceutically acceptable salt or metal complex thereof, in an amount sufficient to stabilize and reverse a vulnerable atherosclerotic plaque and a pharmaceutically acceptable carrier. In some examples, the therapeutic composition can also include an antioxidant, a mineral, a dietary nitrate/nitrite, and/or a vitamin.

An oral dosage form can include a sulfated polysaccharide, or a pharmaceutically acceptable salt or metal complex thereof, in an amount sufficient to stabilize and reverse a vulnerable atherosclerotic plaque and a pharmaceutically acceptable carrier.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 1 is a flow chart of risk classification of carotid plaques based on the size of lipid-rich necrotic core.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a lesion" includes reference to one or more of such materials and reference to "subjecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

The term "dosage unit" or "dose" are understood to mean an amount of an active agent that is suitable for administration to a subject in order achieve or otherwise contribute to a therapeutic effect. In some examples, a dosage unit can refer to a single dose that is capable of being administered to a subject or patient, and that may be readily handled and packed, remaining as a physically and chemically stable unit dose.

As used herein, a "dosing regimen" or "regimen" such as "treatment dosing regimen," or a "prophylactic dosing regimen" refers to how, when, how much, and for how long a dose of an active agent or composition can or should be administered to a subject in order to achieve an intended treatment or effect.

As used herein, the terms "treat," "treatment," or "treating" refers to administration of a therapeutic agent to subjects who are either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition.

As used herein, the terms "therapeutic agent," "active agent," and the like can be used interchangeably and refer to an agent that can have a beneficial or positive effect on a subject when administered to the subject in an appropriate or effective amount.

The phrase "effective amount," "therapeutically effective amount," or "therapeutically effective rate(s)" of an active ingredient refers to a substantially non-toxic, but sufficient amount or delivery rates of the active ingredient, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In some embodiments, at least one ingredient may be an active agent or otherwise have properties that exert physiologic activity when administered to a subject. For example, amniotic fluid includes at least two ingredients (e.g. water and electrolytes) and is itself a composition or formulation.

As used herein, a "subject" refers to an animal. In one aspect the animal may be a mammal. In another aspect, the mammal may be a human.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a *de facto* equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Stabilizing and Reducing Atherosclerotic Lesions

Arteriosclerosis occurs when arteries (i.e. blood vessels that carry oxygen and nutrients from the heart to the rest of the body) become thick and stiff. In some cases, this can restrict blood flow to bodily organs and tissues, depriving them of needed oxygen and nutrients. Atherosclerosis is a specific type of arteriosclerosis that generally refers to the buildup of material in and on artery walls, which can restrict blood flow. This buildup of material can be referred to as an atherosclerotic plaque or lesion and can be formed of a variety of materials, such as cholesterol, fatty substances, cellular waste products, calcium, fibrin, etc.

Depending on the severity of the plaque and the location of plaque formation, atherosclerosis can lead to a number of adverse health conditions, such as coronary heart disease, angina, carotid artery disease, peripheral artery disease, chronic kidney disease, or the like. Further, in some cases, a piece of plaque may break off and be carried by the bloodstream until it gets stuck, or a blood clot may form on the surface of the plaque. In either case, it is possible for the artery to be blocked. If the blocked artery supplies the heart or brain, a heart attack or stroke can occur. If an artery supplying oxygen to the extremities is blocked, gangrene (i.e. tissue death) can occur.

According to the classification by the American Heart Association, atherosclerotic plaques or lesions can be characterized by the severity of the lesion as follows: Type I, adaptive intimal thickening; Type II, fatty streak; Type III, translational or intermediate lesions; Type IV, atheroma; Type V, fibroatheroma or atheroma with thick fibrous cap; and Type VI, complicated plaques with surface defects and/or hematoma-hemorrhage and/or thrombosis as defined in Stary et al, *A Definition of Advanced Types of Atherosclerotic Lesions and a Histological Classification of Atherosclerosis*, A report from the Committee on Vascular Lesions of the Council on Arteriosclerosis, American Heart Association, *Circulation*, 1995; 92: 1355-1374 which is incorporated herein by reference. In some cases, plaque Types IV-VI can be considered vulnerable plaques. More generally, vulnerable plaques can include any plaque at high risk of disruption leading to thrombosis.

Vulnerable plagues are particularly unstable and prone to produce sudden major problems, such as heart attack or stroke. Some of the defining characteristics of vulnerable plaques can include a thin and/or damaged fibrous cap, a large lipid-rich necrotic core, active local inflammation, presence of calcified nodules, intra-plaque hemorrhage, severe stenosis, etc. One or more of these characteristics can contribute to a high mechanical stress zone on the fibrous cap of the atheroma and/or reduce the plaque mechanical strength, which can make it prone to rupture.

It can be somewhat challenging to identify vulnerable atherosclerotic plaques. For example, because artery walls typically enlarge in response to enlarging plaques, these plaques do not usually produce much stenosis of the artery lumen. As such, they are not typically detected by cardiac stress tests or angiography. However, there are a number of imaging methods that can be useful in predicting and identifying vulnerable atherosclerotic plaques. Clinical imaging modalities used to study carotid and coronary artery disease include magnetic resonance imaging (MRI), intravascular ultrasound (IVUS), non-invasive ultrasound imaging, computed tomography, angiography, and optical coherence tomography (OCT) and can be used to identify and characterize vulnerable atherosclerotic plaques.

Conventional non-invasive ultrasound can be used to measure intima-media thickness (IMT) of the carotid artery. The procedure can be performed using a standard ultrasound machine with transducer, with scanning taking place in both transverse and longitudinal planes along the common carotid artery, carotid bulb, and internal carotid artery. Due to noninvasive, portable, and affordable nature, IMT ultrasound is recommended by the American Heart Association for clinical use as an initial risk stratification tool. A comprehensive scan may typically be completed within 30-60 minutes. Results show that echoluency of plaque has been associated with lipid content and plaques investigated by ultrasound can be broadly classified as hard, soft, or mixed. In regard to vulnerable plaque, however, noninvasive ultrasound imaging has not been demonstrated to have the capability to accurately distinguish plaque components including hemorrhage and fibrous cap.

Intravascular ultrasound (IVUS) is an invasive coronary atherosclerotic plaque imaging modality. IVUS is essentially a catheter-mounted ultrasound transducer and follows the same principles regarding ultrasound generation, signal reception, data processing, and image presentation. A grayscale image can be generated based on which plaques can be broadly classified as soft, intermediate, calcified, and mixed. Moreover, added modules can enhance tissue characterization abilities of IVUS, allowing for detection and quantification of different plaque structures. This is achieved, in broad terms, by analyzing, in addition to reflected signal amplitude, its frequency and power.

Regarding vulnerable plaques, IVUS, and its modular expansions, can reliably assess plaque burden, expansive remodeling, as well as presence and relative proportion of necrotic core, calcifications, and neoangiogenesis (contrast enhanced; penetration depth, 5 mm). Confirmation of greater strains in fibroatheromatous, as compared to fibrous plaques, has also been provided by compound ultrasound strain imaging (alternatively known as palpography/elastography). However, at its current form (20/40 MHz transducers), it cannot visualize plaque caps, especially thinner ones (resolution, <100 µm).

Optical coherence tomography (OCT) is another invasive imaging modality that uses near-infrared light (e.g. 1.3 µm in wavelength) in a manner analogous to sonography. Light reflected from plaque structures provides image data whereas the background effect of scattered light is negated through use of interferometric techniques. Bright or dark areas occur as a result of constructive or destructive interference between reflected and reference beams. Given the much smaller wavelength of light in comparison to ultrasound, OCT resolution is 1 order of magnitude higher (~10 µm), allowing for proper visualization of fibrous caps, collagen content (polarization-sensitive OCT), macrophages (related to inflammation), neovessels (appearing as microchannels), ruptures, and thrombi. OCT performance, with regard to microcalcifications at the lower end of the spectrum (<5 µm in diameter), remains uncertain. Consequently, several, but not all, aspects of vulnerability are visualized. OCT limitations include the need for blood displacement, attributed to the high scattering effect of its components, longer image acquisition times (although newer, frequency domain analysis-based processing methods), frequent artifacts, inability to assess deeper plaque structures, as well as relatively poor discrimination between calcified areas and lipid core, given that both appear as signal poor areas (with clear and diffuse borders, respectively).

A newer form of OCT, micro OCT (µOCT), offers axial and lateral resolution in the order of 1 to 2 µm, by means of advanced frequency domain analysis and use of broad bandwidth light, approaching histology levels. Thus, events in the cellular and molecular level, crucial to atherosclerosis development and progression, can be visualized, including leukocyte diapedesis, fibrin strand formation, ECM production, endothelial denudation, microcalcifications and cholesterol crystal formation, and penetration of the fibrous cap.

Computed tomography coronary angiography (CTCA) utilizes a computed tomography (CT) scanner in combination with iodine intravenous dye to visualize the coronary arteries. Significant advantages stem from its very nature: noninvasiveness, ability for imaging the whole coronary vasculature, and potential for assessing both vessel wall in addition to the lumen. Advances in technology have allowed for improved image quality with reduced scan times and radiation exposure. For example, multislice (or multidetector) scanners possess a 2-dimensional detector array allowing for simultaneous acquisition of multiple planar images (slices), reducing examination time and possibility for motion artifacts—those with an array breadth of 160 mm allow for imaging of the heart in a single beat. Use of softer reconstruction kernels leads to improved soft-tissue visualization, however at the expense of spatial resolution. Prospective gating can thus be used in order to synchronize image acquisition with diastole (increased coronary blood flow). Moreover, advent of dual-energy monochromatic scanners may overcome limitations in tissue assessment caused by adjacent intense calcification, by negating the beam-hardening effect. Finally, dual-source scanners may complete the examination in only half a rotation. A related, albeit simpler, technique of calcium scoring does not use an intravenous dye and focuses primarily on coronary calcium quantification to predict the risk for subsequent events.

Regarding vulnerable plaques, CTCA can reliably assess the presence, size, and thickness of the necrotic core, by grading tissue in Hounsfield units (HU; plaques with large cores will cause less attenuation and thus have lower unit values). Specific high-risk plaque criteria have been developed, such as positive remodeling (remodeling index [RI], ≥1.1, also a surrogate for plaque composition), (very) low (given that the threshold for a ≥10% necrotic core is 41 HU) attenuation plaque (LAP; <30 HU), napkin-ring sign (a low attenuation core surrounded by a rim of relatively high attenuation—pathogenesis is still debatable), and presence of spotty calcifications (<3 mm—in accord with the role of calcium specs in destabilizing plaques).

Coronary artery calcium score (CACS) is an alternative parameter measured by means of cardiac CT without the need for intravenous dye. The score is an index of plaque quantity derived from total plaque area and density of calcium lesions. Typically, a subject's CACS is compared to others of similar gender and age to determine a percentile rank. Despite the fact that it only assesses one aspect of atherosclerosis, as opposed to CTCA, it has been proposed that the latter offers additional prognostic information only in patients with intermediate to high CACS.

Magnetic resonance imaging (MRI) also has the ability to visualize the soft-tissue component of atherosclerotic plaques, as well as neovessel formation and diffusion properties (wall permeability). Importantly, MRI can prospectively determine vulnerable plaque features specifically related with (pharmacologically induced) disruption. These features are related to plaque remodeling (with positive remodeling and grater plaque area associated with future rupture) and inflammation indices (markedly increased gadolinium enhancement which denotes increased neovessel permeability and extracellular space expansion, as in intense apoptosis/necrosis). Using multiple pulse sequences such as time-of-flight (TOF) white blood, double inversion recovery (DIR) black blood, and turbo spin echo (TSE) black blood sequences, plaque components such as lipid core, fibrous cap, calcification, hemorrhage, and loose matrix can be delineated. Current limitations include motion artifacts and use in cases of cardiac implants or devices.

Invasive coronary thermography is an approach that aims to detect subtle temperature increases of the vessel wall in areas of heat production, usually accompanying inflamed and/or ruptured atherosclerotic plaques. Purpose-built catheters include hydrofoil and balloon-based designs, ensuring adequate apposition of the thermistor module on the vessel wall. The latter is also able to provide temporary lumen occlusion, thus negating any cooling, convection-based effects of blood flow and accentuating underlying gradients. In some cases, a difference of ≥0.5° C. between plaque and healthy vessel wall can be associated with an increased probability of adverse events.

Less widely used techniques for detecting vulnerable plaque include positron emission tomography (PET), single-photon emission computed tomography (SPECT), nuclear imaging, thermography, angioscopy, hydrogen spectroscopy, intravascular palpography, diffuse reflectance spectroscopy (DRS), intrinsic fluorescence spectroscopy (IFS) Raman spectroscopy (RS), and spectroscopic intravascular photoacoustic imaging (sIVPA).

Additionally, promising new results have been shown in imaging plaque using near-infrared spectroscopy (NIRS) techniques originally developed for neural imaging. However, clinical use of the technology remains in the trial phase. Near-infrared spectroscopy (NIRS) utilizes characteristic emission spectra produced by plaque contents following interaction with photons (wavelength area, 700-2500 nm). Low sensitivity, in terms of induced response, and high penetration, as compared with visible light spectroscopy, render this method appropriate for assessing the lipid content of plaques, especially in cases of positive remodeling, with large, deep-seated, lipid-laden necrotic cores. Studies using NIRS have shown that large lipid content, rather than plaque burden, is associated with thin cap fibroatheroma features. Larger lipid core burden has been shown to accurately differentiate between culprit and non-culprit lesion in ST-elevation MI patients and has been associated with higher risk for periprocedural myocardial infarction. Interestingly, combination with IVUS may allow for concomitant appreciation of both plaque structure and composition, comparing favorably with OCT.

A modified form of NIRS, near-infrared autofluorescence, involves active stimulation of lipid components to emit detectable infrared light. Combination with OCT can allow for better visualization of lipid-laden necrotic cores and, moreover, accurate localization of the area within it with the densest macrophage concentration.

Molecular imaging, including positron emission tomography (PET) and single-photon emission computed tomography (SPECT), involving targeting and visualizing specific components of biological processes can also be used to visualize atherosclerotic plaques to help identify the vulnerable plaque. Classified as nuclear medicine imaging modalities, PET and SPECT provide functional and metabolic information by tracking the movement and accumulation of positron and gamma emitting radioisotope tracers respectively. Theoretically, any modality may be used for molecular imaging as long as a proper tracer can be developed, for example, photon-emitting or possessing paramagnetic properties. Any substance of interest may act as a target provided that it can be either attached to or modified as a tracer. A variety of vulnerability-related processes can be amenable to imaging, including leukocyte adhesion (through involved proteins, such as selectins and vascular cellular adhesion molecule 1 (VCAM-1)), macrophage content (osteopontin), collagen degradation (labeled matrix metalloproteinase [MMP] inhibitors), cell apoptosis (use of annexin that binds to lipids exclusively present in the outer layer of apoptotic cell membrane) or necroptosis (radiolabeled necrostatin, a preferential inhibitor of necroptosis), and neoangiogenesis (use of labeled anti-vascular endothelial growth factor antibodies as tracers).

Beside imaging biomarkers (molecular imaging), circulating or serum biomarkers including locally released biomarkers are also used to help identify vulnerable plaque. These biomarkers are involved in the different stages (i.e., endothelial damage) and processes (i.e., inflammation) of atherosclerotic plaque development and, therefore, are recognized as potential biomarkers of vulnerable plaque. Some of these biomarkers are C-reactive protein (CRP), interleukin-6 (IL-6), interleukin-18 (IL-18), tumor necrosis factor alpha (TNF-α), soluble CD40 ligand (sCD40L), matrix metalloproteinase (MMP), soluble intercellular adhesion molecule (sICAM), soluble vascular cellular adhesion molecule (sVCAM), E-selectin, P-selectin, pregnancy-associated plasma protein-A (PAPP-A), lipoprotein-associated phospholipase $A_2$ (Lp-$PLA_2$), tissue plasminogen activator inhibitor (PAI), myeloperoxidase, fibrinogen, monocyte chemo-attractant protein-1 (MCP-1), neopterin, oxidized LDL, osteopontin (OPN), osteooritegerin (OPG), and microRNAs (miRNAs).

These and other suitable methods can be used to help identify vulnerable atherosclerotic plaques. It is noted that each of these methodologies includes some limitations. As such, in some examples, a combination of one or more of the methods of identification described herein can be used. In some specific examples, identifying a vulnerable atherosclerotic plaque can include CTCA. In some additional specific examples, identifying a vulnerable atherosclerotic plaque can include magnetic resonance imaging (MRI). In some further examples, MRI can include carotid atherosclerotic plaque MRI (CMRI). (See, for example, *Atherosclerotic plaque imaging by carotid MRI*, Zhao, X., Tiller Z. E. & Yuan, C. Curr Cardiol Rep (2009) 11:70 which is incorporated herein by reference.) In some examples, identifying a vulnerable atherosclerotic plaque does not include an invasive technique. Overall, the factors to be considered in determining an ideal imaging method include safety, availability, cost, and effectiveness. When considering such factors, the MRI can often be a particularly effective option to evaluate vulnerability of arterial plaques currently available. It can depict not only the degree of stenosis but also plaques in the arterial wall including lipid-rich necrotic core, fibrous cap, intraplaque hemorrhage, calcification, etc. Contrasted to CT and other methods, MRI imaging does not expose the patient to ionizing radiation and may be performed without the use of intravenously injected contrast agents. MRI-PlaqueView™ is the only FDA approved software currently available to characterize and measure morphology, plaque burden, plaque composition and components of carotid plaque for vulnerability although other similar software may be used.

Current treatments for atherosclerosis include cholesterol medications such as statins, anti-platelet medications, anticoagulants, beta blocker medications, angiotensin-converting enzyme (ACE) inhibitors, calcium channel blockers, diuretics, and other medications. Although such therapies can be valuable, many adverse events continue to occur in patients receiving the best currently available therapy. Further, many of these medications are met with mixed and/or slow results, depending on the subject and the severity of the condition. In particular, vulnerable plaques can be especially challenging to treat. For example, it can generally be challenging to stabilize and reduce a size of an atherosclerotic plaque, especially a vulnerable atherosclerotic plaque. Therefore, there is a need for improved compositions and methods for treating atherosclerotic plaques, including vulnerable atherosclerotic plaques.

The present disclosure describes a number of compositions, dosage forms, and methods that can be used to stabilize atherosclerotic plaques, including vulnerable plaques. In some examples, the compositions, dosage forms, and methods described herein can be used to reduce a size of an atherosclerotic plaque, including vulnerable plaques.

As a further note, in the present disclosure, it is noted that when discussing the compositions, the dosage forms, and the methods, each of these discussions can be considered applicable to each of these examples, whether or not they are explicitly discussed in the context of that example. Thus, for example, in discussing details about the compositions per se, such discussion also refers to the dosage forms and the methods described herein, and vice versa.

In further detail, a therapeutic composition for treating an atherosclerotic plaque, such as a vulnerable atherosclerotic plaque, can include a therapeutically effective amount of a sulfated polysaccharide, or a pharmaceutically acceptable salt or metal complex thereof. In some examples, the therapeutic composition can include a sulfated polysaccharide, or a pharmaceutically acceptable salt or metal complex thereof, in an amount sufficient to reduce a size of the vulnerable atherosclerotic plaque.

Several algal species can possess a variety of therapeutic properties. For example, some algal species include one or more bioactive polysaccharides, such as sulfated polysaccharides. These bioactive polysaccharides can have a variety of therapeutic properties, such as antioxidant, antitumor, immunomodulatory, anti-inflammatory, anticoagulation, antiviral, antiprotozoan, antibacterial, antilipemic, or other bioactive properties. Non-limiting examples of marine algae polysaccharides, including sulfated polysaccharides, can include fucans, fucoidans, carrageenans, furcellaran, ulvans (e.g. rhamnan sulfate), galactans, or the like. In some examples, the composition can include one or more of a sulfated fucan, a fucoidan, a carrageenan, an ulvan, and a sulfated galactan. In some examples, the sulfated polysaccharide can include rhamnan sulfate, fucoidan sulfate, arabinan sulfate, arabinogalactan sulfate, galactan sulfate, mannan sulfate, the like, functional analogues thereof, or a combination thereof. In some examples, the therapeutic composition can include rhamnan sulfate. In some examples, the therapeutic composition can include a fucoidan sulfate. In some examples, the therapeutic composition can include an arabinan sulfate. In some examples, the therapeutic composition can include an arabinogalactan sulfate. In some examples, the therapeutic composition can include a galactan sulfate. In some examples, the therapeutic composition can include a mannan sulfate. In some examples, functional analogues can include natural or synthetic oligosaccharides. Non-limiting examples of functional analogues can include rhamno-oligosaccharides, fuco-oligosaccharides, chito-ologosaccharides, galacto-oligosaccharide, fructo-oligosacchrides, sulfated rhamno-oligosaccharides, sulfated fuco-oligosaccharides, beta-glucans zylo-oligosaccharides, mannan oligosaccharides galacto-mannan-oligosaccharides, rhamnan sulfate oligosaccharides, heparan sulfate oligosaccharides, chondroitin sulfate oligosaccharides, keratan sulfate oligosaccharides, and the like.

It is noted that different varieties of fucans, fucoidans, carrageenans, furcellaran, ulvans, galactans, and the like can be extracted or derived from different species of marine algae. Thus, for example, a fucoidan derived from two different species of brown algae may be somewhat different. Accordingly, sulfated polysaccharides derived or extracted from one species may have more desirable properties than a similar sulfated polysaccharide derived or extracted from another species within the same genus of algae.

With this in mind, in some examples, the sulfated polysaccharide can be extracted or derived from red algae, brown algae, green algae, microalgae, or a combination thereof. In some examples, the sulfated polysaccharide can be extracted or derived from red algae. In some examples, the sulfated polysaccharide can be extracted or derived from brown algae. In some examples, the sulfated polysaccharide can be extracted or derived from green algae. In still other examples, the sulfated polysaccharide can be extracted or derived from microalgae. In some specific examples, the sulfated polysaccharide can include a polysaccharide extracted or derived from algae selected from the group consisting of *Monostroma nitidum, Monostroma latissimum, Monostroma angicava, Ulva lactuca, Enteromorpha intestinalis, Caulerpa* spp., *Codium* spp., *Fucus* spp., *Sargassum vulgare, Sargassum fusiforme, Ecklonia cava, Ecklonia kurome, Laminaria* spp., *Chondrus crispus, Phyllophora brodiei, Grateloupia indica, Amphora coffeaeformis, Codium* spp., and combinations thereof. In some additional examples, the sulfated polysaccharide can be or include a polysaccharide extracted or derived from *Monostroma nitidum*.

Methods of extracting polysaccharides from marine algae are known in the art. As such, these methods will not be discussed in detail. The composition and molecular weight of marine polysaccharides and oligosaccharides can vary with sources. However, they can generally be extracted with a hot water solution following certain pretreatment such as cleaning, drying, milling, demineralization, alkaline treatment, enzymatic treatment, etc. The extracted polysaccharides may be further purified by separation columns and membranes such as size-exclusion chromatography and ion exchange chromatography. For example, commercial carrageenan is extracted from red algae *Eucheuma cottonii*. The fresh seaweed is cleaned and dried. The seaweed is then chopped to 1 cm long before extracted with 50 times (w/w) of water at 50-90° C. for 1 to 5 hours. After extraction, the mixture is centrifuged at 12,000 RPM at 50° C. for 30 minutes. The resulting supernatant is mixed with 2-propanol at a 1:2 ratio to precipitate polysaccharides. The precipitant is recovered and centrifuged to further remove the liquid before being freeze dried for a finished commercial carrageenan product.

Any suitable method of extracting or deriving a bioactive polysaccharide from marine algae can be used to obtain the sulfated polysaccharide of the present therapeutic compositions. Alternatively, some suitable equivalents especially sulfated oligosaccharides can be synthesized rather than extracted from natural sources.

The sulfated polysaccharide can be present in the therapeutic composition in a variety of amounts as long as a therapeutic effect is achieved. In some examples, the sulfated polysaccharide can be present in the therapeutic composition in an amount from about 10% wt % to about 100% wt %. In other examples, the sulfated polysaccharide can be present in an amount from about 20% wt % to about 50% wt %. Unless otherwise indicated, all percentages described herein refer to the amount of the component as a percentage of the total amount of the composition.

In some further examples, the therapeutic composition can also include an antioxidant. In some cases, the antioxidant can help inhibit oxidation of the sulfated polysaccharide or other ingredients in the therapeutic composition. In some examples, the antioxidant can provide a therapeutic effect when administered in connection with the sulfated polysaccharide.

A variety of antioxidants can be used in the therapeutic composition. In some examples, the antioxidant can include butylated hydroxyanisole (BHA), butylated hydroxytoluene (BHT), ascorbic acid, ascorbyl palmitate, alpha-lipoic acid, N-acetyl cysteine, glutathione, carotenoids, coenzyme Q10, trans-resveratrol, tocopherols, tocotrienols, potassium metabisulfite, sodium thiosulfate, alliin, propyl gallate, epigallocatechin gallate, the like, or a combination thereof. In other examples, the antioxidant can include a plant-based powder blend rich in antioxidants such as polyphenols. Antioxidant polyphenols can be effective at reducing oxidative stress and reactive oxygen species (ROS). In the case of cardiovascular disorders, oxidative stress and ROS can cause endothelial damage, progression of atherosclerosis, injury in sustained myocardial infarction and/or in ischemia reperfusion, the like, or a combination thereof. A deterioration in nitric oxide (NO) dependent vasorelaxation is a well-established risk factor that can predispose individuals to cardiovascular disease. Antioxidant polyphenols can help prevent hypercholesterolemia, hypertension, and platelet aggregation, as well as to improve endothelial function and arterial elasticity.

Non-limiting examples of plant-based antioxidant-rich powders can include red grape skin extract, red grape seed extract, white grape skin extract, white grape seed extract, green tea extract, carrot juice or extract, tomato juice or extract, broccoli juice or extract, green cabbage juice or extract, onion juice or extract, garlic juice or extract, asparagus juice or extract, olive juice or extract, cucumber juice or extract, bilberry juice or extract, grapefruit juice or extract, papaya juice or extract, pineapple juice or extract, strawberry juice or extract, apple juice or extract, apricot juice or extract, cherry juice or extract, orange juice or extract, black currant juice or extract, beetroot, kiwi fruit, watermelon, hawthorn berry, celery, cili Fruit, jujube fruit, broccoli, blue honeysuckle fruit, strawberry, yumberry, purple sweet potato, monk fruit, plum, and the like, or a combination thereof.

The antioxidant can be present in the therapeutic composition in a variety of amounts. In some examples, the antioxidant can be present in the therapeutic composition in an amount sufficient to inhibit oxidation of the sulfated polysaccharide. In some examples, the antioxidant can be present in the therapeutic composition in a therapeutically effective amount. In some specific examples, the antioxidant can be present in the composition in an amount from about 10 wt % to about 90 wt %, and in some cases 20 wt % to about 80 wt %.

In some other examples, the therapeutic composition can also include a source of nitrate and/or nitrite. Dietary nitrate and nitrite are precursors of nitric oxide (NO) that plays vital roles in vascular health. In addition to the endothelial nitric oxide synthase, a significant portion of systemic nitric oxide may be generated by reduction of nitrate to nitrite to nitric oxide by other enzymatic systems including the one that exists in the commensal gram-negative bacteria on the tongue. Nitric oxide is a vasodilator that increases blood flow. It also has anti-inflammatory, anticoagulant, antiplatelet, and antioxidant activities in relation to the development of atherosclerosis. It has been shown that dietary nitrate and nitrite lower blood pressure in humans.

The therapeutic composition can include a variety of source of nitrate and nitrite. Non-limiting examples include nitrate and nitrite salts of sodium, potassium, calcium, magnesium, manganese, iron, copper, chromium and zinc. Also many fruits and vegetables are good sources of nitrate and nitrite. A non-exhausting list includes celery, cress, lettuce, chervil, beetroot, spinach, mustard greens, cabbage, fennel, leek, parsley, rocket, swiss chard, leafy chicory, Kohlrabi, radish, etc. Many herbs such as traditional Chinese medicinal herbs also contain an appreciable amount of nitrate and nitrite. They include, but are not limited to, danshen root (*Radix salvia* miltorrhizae), snakegourd fruit (*Fructus trichosanthis*), longstamen onion bulb (*Bulbus allii macrostemi*), sanchi (*Radix notoginseng*), ginseng (*Radix ginseng*), borneol (*Borneolum syntheticum*), and borneol (*Cinnamomum*). In some specific examples, the plant-based nitrate and nitrite can include a blend of powdered extracts. In still other examples, the plant-based nitrate and nitrite can include a blend of liquid extracts or juices In some examples, the nitrate and nitrite can be present in the therapeutic composition in an amount from about 10 wt % to about 90 wt %. In other examples, the nitrate and nitrite can be present in an amount from about 20 wt % to about 80 wt %.

In some additional examples, the therapeutic composition can include a source of magnesium. Magnesium supplementation can improve myocardial metabolism, can inhibit calcium accumulation and myocardial cell death, can improve vascular tone, peripheral vascular resistance, afterload and cardiac output, can reduce cardiac arrhythmias, can improve lipid metabolism, among others. Magnesium can also reduce vulnerability to oxygen-derived free radicals, improve human endothelial function, and inhibit platelet function, including platelet aggregation and adhesion.

The therapeutic composition can include a variety of source of magnesium. Non-limiting examples, can include magnesium oxide, magnesium citrate, magnesium orotate, magnesium chloride, magnesium lactate, magnesium sulfate, magnesium carbonate, magnesium glycinate, magnesium malate, magnesium taurate, the like, or a combination thereof. In addition, magnesium can be chemically attached to sulfated polysaccharides via an ionic or a coordination bond or a combination of both. The resulting magnesium polysaccharide complexes such as magnesium rhamnan sulfate complex will have many advantages over a physical mixture of a magnesium salt and rhamnan sulfate in the therapeutic composition.

Magnesium can be present in the therapeutic composition in a variety of amounts. In some examples, magnesium can be present in the composition an amount from about 10 wt % to about 90 wt %. In yet other examples, magnesium can be present in the composition in an amount from about 20 wt % to about 80 wt %. Complimentary complexes of zinc, copper, iodine, iron, calcium, manganese, molybdenum, boron or the like can also be used instead of magnesium in the above examples.

The therapeutic composition can also include a source of vitamin K2 menaquinone. High intake of vitamin K2 has been shown to be associated with lower prevalence of arterial calcification and coronary heart disease mortality. Vitamin K2 activates matrix gla-protein (MGP) in the vascular endothelium that inhibits arterial calcification.

The therapeutic composition can include a variety of forms of vitamin K2. Non-limiting examples can include menaquinone-2 (MK-2), MK-3, Mk-4, MK-5, MK-6, MK-7, MK-8, MK-9, MK-10, MK-11, MK-12, MK-13, and MK-14. Vitamin K2 can be present in the therapeutic composition in a variety of amounts. In some examples, vitamin K2 can be present in the composition in an amount from about 10 μg to about 100,000 μg. In yet other examples, vitamin K2 can be present in the composition from about 50 μg to 500 μg.

The therapeutic composition can also include a pharmaceutically acceptable carrier. The nature of the pharmaceutically acceptable carrier can depend on the intended mode of administration. In some examples, the therapeutic composition can be formulated for administration via injection. In other examples, the therapeutic composition can be formulated for oral administration. In yet another example, the therapeutic composition can be formulated for IV administration.

Where the therapeutic composition is formulated for administration via injection, the pharmaceutically acceptable carrier can include one or more components suitable for such a composition. Non-limiting examples can include water, a solubilizing or dispersing agent, a tonicity agent, a pH adjuster or buffering agent, a preservative, a chelating agent, a bulking agent, the like, or a combination thereof.

In some examples, an injectable therapeutic composition can include a solubilizing or dispersing agent. Non-limiting examples of solubilizing or dispersing agents can include polyoxyethylene sorbitan monooleates, lecithin, polyoxyethylene polyoxypropylene co-polymers, propylene glycol, glycerin, ethanol, polyethylene glycols, sorbitol, polyethoxylated castor oils, cyclodextrins, caboxymethyl cellulose, acacia, gelatin, methyl cellulose, polyvinyl pyrrolidone, the like, or combinations thereof.

In some examples, an injectable therapeutic composition can include a tonicity agent. Non-limiting examples of tonicity agents can include sodium chloride, potassium chloride, calcium chloride, magnesium chloride, mannitol, sorbitol, dextrose, glycerin, propylene glycol, ethanol, trehalose, phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, and BSS Plus, the like, or combinations thereof. The tonicity agent can be used to provide an appropriate tonicity of the therapeutic composition. In one aspect, the tonicity of the therapeutic composition can be from about 250 to about 350 milliosmoles/liter (mOsm/L). In another aspect, the tonicity of the therapeutic composition can be from about 277 to about 310 mOsm/L.

In some examples, an injectable therapeutic composition can include a pH adjuster or buffering agent. Non-limiting examples of pH adjusters or buffering agents can include a number of acids, bases, and combinations thereof, such as hydrochloric acid, phosphoric acid, citric acid, sodium hydroxide, potassium hydroxide, calcium hydroxide, acetate buffers, citrate buffers, tartrate buffers, phosphate buffers, the like, or combinations thereof. Typically, the pH of the therapeutic composition can be from about 5 to about 9, or from about 6 to about 8.

In some examples, an injectable therapeutic composition can include a preservative. Non-limiting examples of preservatives can include ascorbic acid, acetylcysteine, bisulfate, metabisulfite, monothioglycerol, phenol, meta-cresol, benzyl alcohol, propyl paraben, butyl paraben, benzalkonium chloride, benzethonium chloride, butylated hydroxyl toluene, myristyl gamma-picolinium chloride, 2-phenoxyethanol, phenyl mercuric nitrate, chlorobutanol, thimerosal, tocopherols, the like, or combinations thereof.

In some examples, an injectable therapeutic composition can include a chelating agent. Non-limiting examples of chelating agents can include ethylenediaminetetra acetic acid, calcium, calcium disodium, diethylenetriaminepenta acetic acid, the like, or combinations thereof.

In some examples, an injectable therapeutic composition can include a bulking agent. Non-limiting examples of bulking agents can include sucrose, lactose, trehalose, mannitol, sorbitol, glucose, rafinose, glycine, histidine, polyvinyl pyrrolidone, the like, or combinations thereof.

Where the therapeutic composition is formulated for oral administration, the pharmaceutically acceptable carrier can include one or more components suitable for such a composition. In the case of solid oral compositions or dosage forms, the pharmaceutically acceptable carrier can include a variety of components suitable for forming a capsule, tablet, or the like. In the case of a liquid oral composition or dosage form, the pharmaceutically acceptable carrier can include a variety of components suitable for forming a dispersion, a suspension, a syrup, an elixir, or the like.

In some specific examples, the therapeutic composition can be formulated as a tablet. In such examples, the therapeutic composition can typically include a binder. Non-limiting examples of binders can include lactose, calcium phosphate, sucrose, corn starch, microcrystalline cellulose, gelatin, polyethylene glycol (PEG), polyvinyl pyrrolidone (PVP), hydroxypropyl cellulose, hydroxyethylcellulose, carboxymethyl cellulose (CMC), cellulose, other cellulose derivatives, the like, or combinations thereof.

Where the therapeutic composition is formulated as a tablet, in some examples the therapeutic composition can also include a disintegrant. Non-limiting examples of disintegrants can include crosslinked PVP, crosslinked CMC, modified starch, sodium starch glycolate, the like, or combinations thereof.

In some examples, the tablet can also include a filler. Non-limiting examples of fillers can include lactose, dicalcium phosphate, sucrose, microcrystalline cellulose, the like, or combinations thereof.

In some further examples, the tablet can include an exterior coating. Such coatings can be formed with a variety of materials, such as hydroxypropyl methylcellulose (HPMC), shellac, zein, various polysaccharides, various enterics, the like, or combinations thereof.

In some examples, the tablet can include a variety of other ingredients, such as anti-adherents (e.g. magnesium stearate, calcium stearate, for example), colorants (e.g. titanium dioxide, carmine, for example), glidants (e.g. fumed silica, talc, magnesium carbonate, for example), lubricants or anti-caking agents (e.g. talc, silicon dioxide, magnesium stearate, calcium stearate, stearic acid, for example) preservatives, desiccants, and/or other suitable tablet excipients, as desired.

In some other examples, the therapeutic composition can be formulated as a capsule. In such examples, the capsule itself can typically include gelatin, hypromellose, HPMC, CMC, other plant-based capsule materials, the like, or combinations thereof. A variety of excipients can also be included within the capsule, such as binders, disintegrants, fillers, glidants, anti-caking agents, preservatives, coatings, the like, or combinations thereof, such as those listed above with respect to tablets, for example, or other suitable variations.

In some examples, the therapeutic composition can be formulated as a liquid therapeutic composition or liquid oral dosage form. A liquid oral dosage form can include a variety of excipients, such as a liquid vehicle, a solubilizing agent, a thickener or dispersant, a preservative, a tonicity agent, a pH adjuster or buffering agent, a sweetener, the like, or a combination thereof. Non-limiting examples of liquid vehicles can include water, ethanol, glycerol, propylene glycol, the like, or combinations thereof. Non-limiting examples of solubilizing agents can include banzalkonium chloride, benzethonium chloride, cetylpyridinium chloride, docusate sodium, nonoxynol-9, octoxynol, polyoxyethylene polyoxypropylene co-polymers, polyoxyl castor oils, polyoxyl hydrogenated castor oils, polyoxyl oleyl ethers, polyoxyl cetylstearyl ethers, polyoxyl stearates, polysorbates, sodium lauryl sulfate, sorbitan monolaurate, sorbitan monooleate, sorbitan monopalmitate, sorbitan monostearate, tyloxapol, the like, or combinations thereof. Non-limiting examples of thickeners or dispersants can include sodium alginate, methylcellulose, hydroxyethylcellulose, hydroxypropylcellulose, HPMC, CMC, microcrystalline cellulose, tragacanth, xanthan gum, bentonite, carrageenan, guar gum, colloidal silicon dioxide, the like, or combinations thereof. The preservative, tonicity agent, pH adjuster or buffering agent can typically be any of those described above with respect to the injectable formulations or other suitable preservative, tonicity agent, pH adjuster or buffering agent. Sweeteners can include natural and/or artificial sweeteners, such as sucrose, glucose, fructose, stevia, erythritol, xylitol, aspartame, sucralose, neotame, acesulfame potassium, saccharin, advantame, sorbitol, the like, or combinations thereof, for example.

In some examples, the therapeutic composition can be formulated as a functional food product such as a food bar, powder, or beverage. Food bars can be formulated to fit different dietary regiments for any specific purposes such as weight loss, energy, meal replacement, high protein, high fiber, low glycemic, etc. A food bar usually contains ingredients that supply energy-yielding nutrients such as carbohydrate, protein and lipid as well as other macro- and micronutrients including but not limited to vitamins and minerals. Other health promoting ingredients such as fruit and vegetable powder, dietary fibers, pre- and probiotics, antioxidants, other phytochemicals and metabolic modulators may be included in the formulation in addition to filler, binder, emulsifier, water, humectant, flavor, color, sweetener, preservative, etc. The therapeutic composition can be formulated into a food bar with other ingredients to achieve desirable health benefits, taste, texture, flavor and stability. Similarly, the therapeutic composition may be formulated into a powder such as a protein powder, meal replacement powder, or functional beverage dry mix. It can also be formulated into a functional drink. A ready to drink beverage may contain other ingredients including various nutrients, health promoting agents, pH adjustor (acidity regulator), electrolyte, flavor, sweetener, stabilizing agent, color, preservative, etc.

In some examples, the therapeutic composition can be formulated as a medical food (as defined in section 5(b)(3) of the Orphan Drug Act (21 U. S.C. 360ee(b)(3))) to be consumed or administered enterally under the supervision of a physician and which is intended for the specific dietary management of atherosclerosis.

The present disclosure also describes oral dosage forms. The oral dosage forms can include a sulfated polysaccharide, or a pharmaceutically acceptable salt or metal complex thereof, in an amount sufficient to reduce a vulnerability of an atherosclerotic plaque, such as a vulnerable atherosclerotic plaque. The oral dosage form can also include a pharmaceutically acceptable carrier.

The types of sulfated polysaccharides that can be included in the oral dosage forms are generally described above with respect to the therapeutic compositions. In some examples, the oral dosage form can include sulfated polysaccharides in an amount from about 15 mg to about 15,000 mg of sulfated polysaccharides per dose. In some other examples, the oral dosage form can include from about 50 mg to about 1000 mg of sulfated polysaccharides per dose. In some additional examples, the oral dosage form can include from about 30 mg to about 300 mg of sulfated polysaccharides per dose. In still other examples, the oral dosage form can include from about 50 mg to about 200 mg of sulfated polysaccharides per dose.

In some additional examples, the oral dosage forms can include an antioxidant, as described above with respect to the therapeutic compositions. In some examples, the oral dosage form can include the plant antioxidant in an amount from about 20 mg to about 20,000 mg per dose. In other examples, the antioxidant can be present in the oral dosage form in an amount from about 100 mg to about 600 mg per dose. In still other examples, the antioxidant can be present in the oral dosage form in an amount from about 125 mg to about 350 mg per dose. In some specific examples, the antioxidant can be included in the oral dosage form in the form of a powdered blend of edible plant materials with antioxidant activity, such as those described above. In other examples, the antioxidant can be included in the oral dosage form in the form of a liquid blend of edible plant materials with antioxidant activity, such as those described above.

In some additional examples, the oral dosage forms can include a source of nitrate and nitrite, as described above with respect to the therapeutic compositions. In some examples, the oral dosage form can include nitrate and nitrite in an amount from about 20 mg to about 2,000 mg per dose. In other examples, nitrate and nitrite can be present in the oral dosage form in an amount from about 50 mg to about 1,000 mg per dose. In still other examples, nitrate and nitrite can be present in the oral dosage form in an amount from about 200 mg to about 600 mg per dose. In some specific examples, nitrate and nitrite can be included in the oral dosage form in the form of a powdered blend of edible plant materials with nitrate and nitrite, such as those described above. In other examples, nitrate and nitrite can be included in the oral dosage form in the form of a liquid blend of edible plant materials with nitrate and nitrite, such as those described above.

In some additional examples, the oral dosage forms can include magnesium, as described above with respect to the therapeutic compositions. In some examples, magnesium can be included in the oral dosage form in an amount of from about 10 mg to about 1000 mg per dose. In other examples, magnesium can be included in the oral dosage form in an amount of from about 25 mg to about 400 mg per dose.

In some additional examples, the oral dosage forms can include vitamin K2, as described above with respect to the therapeutic compositions. In some examples, vitamin K2 can be included in the oral dosage form in an amount of from about 10 µg to about 100,000 µg per dose. In other examples, magnesium can be included in the oral dosage form in an amount of from about 50 µg to about 500 µg per dose.

In some specific examples, the oral dosage forms can be solid oral dosage forms. Where this is the case, the solid oral dosage forms can include any pharmaceutically acceptable carrier components suitable for a solid oral dosage form. In some specific examples, the solid oral dosage form can include one or more of a binder, a disintegrant, a filler, an anti-adherent, a colorant, a glidant, a lubricant or anti-caking agent, a preservative, a desiccant, the like, or a combination thereof, such as those described above with respect to the therapeutic compositions. In some examples, the solid oral dosage form can be formulated as a tablet. In other examples, the solid oral dosage form can be formulated as a two-piece hard capsule or a hermetically sealed softgel capsule.

In some additional specific examples, the oral dosage forms can be liquid oral dosage forms. Where this is the case, the liquid oral dosage forms can include any pharmaceutically acceptable carrier components suitable for a liquid oral dosage form. In some specific examples, the liquid oral dosage form can include a liquid vehicle, a solubilizing agent, a thickener or dispersant, a preservative, a tonicity agent, a pH adjuster or buffering agent, a sweetener, the like, or a combination thereof, such as those described above.

In some examples, the dosage forms or therapeutic compositions described herein can be disposed in a suitable container. Such containers can include multiple-use containers or single use containers. Non-limiting examples can include bottles, vials, blister packs, bags, or the like. In some examples, the container can be an amber colored container or other suitable container configured to protect the dosage form or therapeutic composition from light. In yet other examples, the container can include instructions and dosing information for the dosage form or therapeutic composition. The container can include a variety of materials, such as polyethylene, polypropylene, polycarbonate, polyvinyl chloride, glass, the like, or a combination thereof.

In yet additional alternatives, the therapeutic compositions described herein can be used as a food additive to fortify a food supply for general population. For example, the therapeutic composition can be safely introduced into a systemic food supply such as, but not limited to, milled grain flours, pastas, breakfast cereals, bread, soup or soup mixes, food bars, spices, condiments, dairy products, beverages, drink mixes, frozen food items, pastries, cookies and crackers, snacks, or the like.

The present disclosure also describes a method of treating a vulnerable atherosclerotic plaque. The method can include identifying the vulnerable atherosclerotic plaque and administering a sulfated polysaccharide, or a pharmaceutically acceptable salt thereof, to a subject in an amount and at a frequency sufficient to stabilize and reverse a vulnerable atherosclerotic plaque.

It is noted that identifying a vulnerable atherosclerotic plaque can be performed before and/or after administering the sulfated polysaccharide. Further, in some examples, identifying a vulnerable atherosclerotic plaque can further include monitoring the vulnerable atherosclerotic plaque over a period of time. Such monitoring can help determine whether or not the vulnerable atherosclerotic plaque has been stabilized and/or reduced in size. Reduction in vulnerability can be manifest via a change in one or more lesion or plaque risk properties. These risk properties can include, but are not limited to, reduction in overall plaque size and artery stenosis (or increase in lumen size), reduction in a lipid-rich necrotic core size, reduction in active inflammation and platelet aggregation, partial or complete repair of an ulcerated thin fibrous cap, reduction in total area of calcified nodules, reduction in total area of hemorrhage, and the like.

Administration of the sulfated polysaccharide, or a pharmaceutically acceptable salt or metal complex thereof, to a subject can be performed in a number of ways. In some examples, the sulfated polysaccharide, or a pharmaceutically acceptable salt or metal complex thereof, can be administered orally. Oral administration can include administration as a solid oral dosage form (e.g. a tablet, a capsule, etc.) or a liquid oral dosage form (e.g. a solution, a suspension, a syrup, an elixir, a gel, etc.). in some other examples, administration can be performed via injection (e.g. intravenous, intra-arterial, intramuscular, sub-cutaneous, etc.). Further, where the sulfated polysaccharide is administered via injection, it can be injected via a bolus injection or via metered infusion. Other forms of administration can also include topical administration, transdermal administration, inhalation, ophthalmic administration, nasal administration, otic administration, administration as a suppository, or the like.

The particular sulfated polysaccharide administered can be any of those described herein, or the like. Further, in some examples, the sulfated polysaccharide can be administered as a composition or dosage form, such as those described herein. In some examples, the sulfated polysaccharide can be administered in an amount from about 15 mg to about 15,000 mg per dose. In some other examples, the oral dosage form can be administered in an amount from about 50 mg to about 1000 mg of sulfated polysaccharides per dose. In some additional examples, the oral dosage form can be administered in an amount from about 30 mg to about 300 mg of sulfated polysaccharides per dose. In still other examples, the oral dosage form can be administered in an amount from about 50 mg to about 200 mg of sulfated polysaccharides per dose. It is also noted that where the sulfated polysaccharide is administered as part of a solid oral dosage form, a dose can include one, two, three, four, or more capsules, tablets, etc.

The sulfated polysaccharide, or a pharmaceutically acceptable salt or metal complex thereof, can be administered at a variety of frequencies. In some examples, a dose of the sulfated polysaccharide can be administered at a frequency of from once daily to four times daily. In some examples, a dose of the sulfated polysaccharide can be administered once per day, twice per day, three times per day, four times per day, or more. In other examples, the sulfated polysaccharide, or a pharmaceutically acceptable salt thereof, can be administered at a frequency of from about once every two days, three days, five days, or seven days, for example. Thus, a variety of suitable administration frequencies can be employed with the present methods.

Further, administration of the sulfated polysaccharide, or a pharmaceutically acceptable salt or metal complex thereof can continue for a variety of durations, depending on the desired treatment outcome. In some examples, administration can continue while symptoms of a vulnerable atherosclerotic condition persist. In other examples, administration can be ongoing as either a prophylactic or intervention treatment. In still other examples, administration can continue until the vulnerable atherosclerotic plaque has been stabilized and/or reduced in size by a predetermined amount. Other suitable durations of administration can also be employed, as desired. As a general guideline, administration duration can be from about 2 weeks to about 24 months, and often from 2 months to 12 months. Similarly, within the administration duration volume reduction of lipid-rich necrotic core from about 5% to about 80%, and in some cases 10% to 90% can be achieved.

In some examples, the sulfated polysaccharide can be administered in connection (e.g. co-administered) with a second active agent. In some examples, the second active agent can include an antioxidant, nitrate, nitrite, magnesium, vitamin K2 or a combination thereof, as described elsewhere herein.

Administration of the sulfated polysaccharide, or a pharmaceutically acceptable salt or metal complex thereof, can provide a number of therapeutic benefits. For example, in some cases, administration can rapidly stabilize and/or reverse atherosclerotic lesions (e.g. vulnerable atherosclerotic lesions) in human arteries. In some examples, administration (e.g. daily administration, for example) can cause rapid reduction in the size of a lipid-rich necrotic core in an atherosclerotic lesion. In some examples, administration (e.g. daily administration, for example) can cause rapid reversal and/or reduction of active inflammation in an atherosclerotic plaque. In some examples, administration (e.g. daily administration, for example) can cause rapid reversal and/or reduction of superficial platelet aggregation of an atherosclerotic plaque. In some examples, administration (e.g. daily administration, for example) can repair and/or strengthen an ulcerated thin fibrous cap on an atherosclerotic lesion. In some examples, administration (e.g. daily administration, for example) can induce rapid reduction of calcified nodules in an atherosclerotic plaque. In some examples, administration (e.g. daily administration, for example) can heal or ameliorate an intraplaque hemorrhage. In some examples, administration (e.g. daily administration, for example) can induce rapid reversal and/or reduction of an atherosclerotic plaque. In some examples, administration (e.g. daily administration, for example) can significantly increase arterial lumen size and reduce artery stenosis at a situs of the atherosclerotic plaque.

In some specific examples, the sulfated polysaccharide can be administered in an amount and at a frequency to reduce a size of lipid-rich necrotic core in a vulnerable atherosclerotic lesion by at least 10% by volume. In other examples, the sulfated polysaccharide can be administered in an amount and at a frequency to reduce a size of lipid-rich necrotic core in a vulnerable atherosclerotic lesion by at least 30% by volume. In still other examples, the sulfated polysaccharide can be administered in an amount and at a frequency to reduce a size of lipid-rich necrotic core in a vulnerable atherosclerotic lesion by at least 50% by volume. In still further examples, the sulfated polysaccharide can be administered in an amount and at a frequency to reduce a size of lipid-rich necrotic core in a vulnerable atherosclerotic lesion by at least 60% by volume. Notably, a total number of calcified nodules in the vulnerable plaque can be reduced by at least 10%, and in some cases 10% to 30%. Similarly, in some cases, a total volume of hemorrhage in the vulnerable plaque can be reduced by at least 10%, and in some cases 10% to 40%. In yet another aspect, artery wall thickness and artery stenosis at the vulnerable plaque can be reduced by at least 5%, while a lumen size may be increased by at least 5%, and in some cases 10% to 40%.

It is also noted that the present methods can be used to treat a number of adverse health conditions related to atherosclerotic plaques (e.g. vulnerable atherosclerotic plaques). Non-limiting examples of adverse health conditions can include coronary heart disease, myocardial infarction, carotid artery disease, stroke, peripheral artery disease, aneurysms, chronic kidney disease, erectile dysfunction, hypertension, Alzheimer's disease, vascular dementia, diabetes, Raynaud's disease, sleep apnea, the like, or a combination thereof.

EXAMPLE 1

In one study, human subjects were prescreened by non-invasive ultrasound imaging of carotid intima media thickness (CIMT). Abnormal CIMT values are indicative of the presence of carotid plaque and increased risk of cardiovascular diseases. Different guidelines and reference ranges for CIMT exist. The European Society of Cardiology (ESC)/European Society of Hypertension (ESH) Guidelines (2013), for example, define asymptomatic damage at 0.9 mm. On the other hand, The American Society of Echocardiography (ASE) recommends that IMT≥75th percentile is considered high and indicative of increased cardiovascular risk. Literature suggests the normal values of CIMT range from 0.5 mm for young to 1.2 mm for old (80+ years). In our study, subjects with CIMT greater than 1.2 mm were selected for further screening of potential vulnerable carotid plaques.

The selected subjects were then scanned with magnetic resonance imaging (MRI) and their vulnerable carotid plaques were identified and analyzed with MRI-PlaqueView, an FDA cleared plaque characterization product for quantitative analysis of atherosclerotic carotid arteries by VPDiagnostics (Seattle, Wash.). Vulnerable plaques are those plaques prone to thrombotic complications and rapid progression, thus causing acute vascular events or death. They are mostly rupture prone plaques from a diagnostic point of view and are identified with specific morphological and compositional features by imaging technology such as MRI. A large lipid-rich necrotic core with a thin fibrous cap is the most noticeable destabilizing feature of plaques. FIG. 1 illustrates risk classification based on the size of lipid-rich necrotic core by MRI-PlaqueView. CAS2, CAS3 and CAS4 indicate vulnerable plaques with different degree because of the presence of distinctive lipid rich necrotic core at least 5% of the plaque(s) by volume. The presence of ulcerated (incomplete) fibrous cap, calcified specs and nodules, and hemorrhage individually or in any combination increases plaque's vulnerability at each CAS (Carotid Atherosclerosis Score). For example, CAS2 with hemorrhage is also considered high risk.

Human subjects identified with vulnerable plaques were orally given a hard capsule containing 150 mg of an extract of *Monostroma nitidum* at approximately 50% rhamnan sulfate blended with 200 mg of a plant-based antioxidant-rich powder, twice daily, for 2 months. The lipid-rich necrotic core volume in their carotid artery was measured at baseline and after the two-month treatment. At the end of the two-month test period, the lipid-rich necrotic core size of individual plaques was reduced 55.5% on average, stabilizing the plaques and making them much less vulnerable or prone to rapture. Lumen size was increased by more than 23%, indicating a reduction in plaque size and artery stenosis in addition to reduction of the lipid-rich necrotic core. It is widely accepted that stabilization and reversal of vulnerable plaque occurs by removal of lipids and necrotic material, triggering endothelial repair and lesion healing.

These results are dramatically superior to those achieved by current interventions, such as statins. In a human clinical study, for example, 33 patients treated with low (5 mg/day) or high (40/80 mg/day) doses of rosuvastatin for 24 months. Analyzed by the same MRI-PlaqueView technology, lipid-rich necrotic core in all patients reduced by about 25% (27% and 19% for low and high dose respectively) at the end of the study. The lumen size and, hence, artery stenosis showed virtually no change. Similar results were reported in another study after 33 patients were treated with atorvastatin (10-80 mg/day) for 3 years. Other published studies on statins showed even less reduction of lipid-rich necrotic core in carotid plaques. Therefore our results have been viewed as surprising and unexpected by those skilled in the art of atherosclerotic care.

EXAMPLE 2

A composition was prepared with 300 mg of an extract of *Monostroma nitidum* at approximately 50% rhamnan sulfate blended with 150 mg of a plant-based antioxidant-rich powder in a hard capsule. The composition was administered twice a day by mouth.

EXAMPLE 3

A composition was prepared with 100 mg fucoidan sulfate 75% extracted from *Laminaria japonica* with a 10,000 mg of fruit and vegetable powder blend (beetroot, kiwi fruit, watermelon, hawthorn berry, celery, cili fruit, jujube fruit, broccoli, blue honeysuckle fruit, whole grape, strawberry, yumberry, purple sweet potato, monk fruit, and plum) that contains about 500 mg of dietary nitrate in a dry beverage mix. This composition was administered once a day.

What is claimed is:

1. A method of treating a vulnerable atherosclerotic plaque, comprising:
    identifying the vulnerable atherosclerotic plaque; and
    orally administering a sulfated polysaccharide, or a pharmaceutically acceptable salt or metal complex thereof, to a subject in an amount and at a frequency sufficient to stabilize and reverse a vulnerable atherosclerotic plaque, wherein the sulfated polysaccharide is a polysaccharide extracted from marine algae of *Monostroma nitidum* and is present as rhamnan sulfate at about 50%, and wherein one or more of:
        a lipid-rich necrotic core in the vulnerable atherosclerotic plaque is reduced in volume by at least 10%;
        active inflammation at the vulnerable atherosclerotic plaque is reduced by at least 10% as measured by an inflammatory biomarker specific to vascular endothelium damage;
        an ulcerated thin fibrous cap on a surface of the vulnerable atherosclerotic plaque is partially or fully repaired and healed;
        a total number of calcified nodules in the vulnerable atherosclerotic plaque is reduced by at least 10%;
        a total volume of hemorrhage in the vulnerable atherosclerotic plaque is reduced by at least 10%;
        an artery wall thickness in the vulnerable atherosclerotic plaque is reduced by at least 10%;
        a lumen size at the vulnerable atherosclerotic plaque is increased by at least 5%; and
        a stenosis at the vulnerable atherosclerotic plaque is reduced by at least 5%.

2. The method of claim 1, wherein the sulfated polysaccharide is administered in an amount from about 50 mg to about 1000 mg per dose.

3. The method of claim 1, wherein administering is performed at a frequency of from once daily to four times daily.

4. The method of claim 1, further comprising orally administering to the subject, a second active agent with the sulfated polysaccharide.

5. The method of claim 4, wherein the second active agent comprises a plant based antioxidant-rich powder.

6. The method of claim 5, wherein the plant based antioxidant-rich powder is administered in an amount of from about 100 mg to about 600 mg per dose.

7. The method of claim 1, wherein identifying comprises at least one of magnetic resonance imaging (MRI), intravascular ultrasound (IVUS), non-invasive ultrasound imaging, computed tomography, angiography, and optical coherence tomography (OCT).

8. The method of claim 1, wherein identifying comprises magnetic resonance imaging.

9. A method of treating a vulnerable atherosclerotic plaque, comprising:
    identifying the vulnerable atherosclerotic plaque;
    orally administering a sulfated polysaccharide, or a pharmaceutically acceptable salt or metal complex thereof, to a subject in an amount and at a frequency sufficient to stabilize and reverse a vulnerable atherosclerotic plaque, wherein the sulfated polysaccharide is a polysaccharide extracted from marine algae of *Monostroma nitidum* and is present as rhamnan sulfate at about 50%; and
    orally administering to the subject, a second active agent with the sulfated polysaccharide.

10. The method of claim 9, wherein the second active agent comprises a plant based antioxidant-rich powder.

11. The method of claim 10, wherein the plant based antioxidant-rich powder is administered in an amount of from about 100 mg to about 600 mg per dose.

12. The method of claim 9, wherein identifying comprises at least one of magnetic resonance imaging (MRI), intravascular ultrasound (IVUS), non-invasive ultrasound imaging, computed tomography, angiography, and optical coherence tomography (OCT).

13. The method of claim 9, wherein identifying comprises magnetic resonance imaging.

14. The method of claim 9, wherein the sulfated polysaccharide is administered in an amount from about 50 mg to about 1000 mg per dose.

15. The method of claim 9, wherein administering is performed at a frequency of from once daily to four times daily.

16. A method of treating a vulnerable atherosclerotic plaque, comprising:
  identifying the vulnerable atherosclerotic plaque using at least one of magnetic resonance imaging (MRI), intravascular ultrasound (IVUS), non-invasive ultrasound imaging, computed tomography, angiography, and optical coherence tomography (OCT); and
  orally administering a sulfated polysaccharide, or a pharmaceutically acceptable salt or metal complex thereof, to a subject in an amount and at a frequency sufficient to stabilize and reverse a vulnerable atherosclerotic plaque, wherein the sulfated polysaccharide is a polysaccharide extracted from marine algae of *Monostroma nitidum* and is present as rhamnan sulfate at about 50%.

17. The method of claim 16, wherein identifying comprises magnetic resonance imaging.

18. The method of claim 16, further comprising orally administering to the subject, a second active agent with the sulfated polysaccharide, wherein the second active agent comprises a plant based antioxidant-rich powder.

19. The method of claim 16, wherein the sulfated polysaccharide is administered in an amount from about 50 mg to about 1000 mg per dose.

20. The method of claim 16, wherein administering is performed at a frequency of from once daily to four times daily.

* * * * *